(12) United States Patent
Chiang et al.

(10) Patent No.: US 8,258,104 B2
(45) Date of Patent: Sep. 4, 2012

(54) METHOD AND COMPOSITION FOR TREATING ALLERGIC DISEASES

(75) Inventors: Bor-Luen Chiang, Taipei (TW); Chung-Sheng Huang, Toorak (AU)

(73) Assignee: Wholesome Biopharm Pty Ltd., Toorak (AU)

( * ) Notice: Subject to any disclaimer, the term of this patent is extended or adjusted under 35 U.S.C. 154(b) by 563 days.

(21) Appl. No.: 12/282,398

(22) PCT Filed: Mar. 14, 2006

(86) PCT No.: PCT/AU2006/000335
§ 371 (c)(1),
(2), (4) Date: Nov. 12, 2008

(87) PCT Pub. No.: WO2007/104070
PCT Pub. Date: Sep. 20, 2007

(65) Prior Publication Data
US 2009/0054360 A1    Feb. 26, 2009

(51) Int. Cl.
*A61K 31/70* (2006.01)
(52) U.S. Cl. .......................................................... 514/43
(58) Field of Classification Search .................. 514/43
See application file for complete search history.

(56) References Cited

U.S. PATENT DOCUMENTS

| | | | |
|---|---|---|---|
| 5,240,694 A | 8/1993 | Gwaltney et al. | |
| 5,290,540 A | 3/1994 | Prince et al. | |
| 6,063,772 A | 5/2000 | Tam | |
| 6,919,331 B2 * | 7/2005 | Yu et al. | 514/223.2 |
| 7,291,331 B1 * | 11/2007 | Croft et al. | 424/130.1 |

FOREIGN PATENT DOCUMENTS

| | | |
|---|---|---|
| CN | 1222351 | 7/1999 |
| CN | 1698644 A | 11/2005 |

OTHER PUBLICATIONS

Database WPI Section Ch, Week 199646 Thomson Scientific London, GB; AN 1999-541091 & CN 1222351A (Chen, Z.) Jul. 14, 1999.
Salvi, S.S., et al. "The Anti-Inflammatory Effects of Leukotriene-Modifying Drugs and Their Use in Asthma" Chest, May 2001, vol. 119, nr. 5, pp. 1533-1546.
Brik, R., et al.; "An Epidemic of Respiratory Syncytial Virus Bronchiolitis Among Infants in Northern Israel;" Journal of the Israel Medical Association; vol. 130, No. 3; Feb. 1, 1996; pp. 222-223.
Chehab, M.S., et al.; "Overview of Bronchiolitis;" Saudi Med J; vol. 26; 2005; pp. 177-190.
Black, C.P.; "Systematic Review of the Biology and Medical Management of Respiratory Syncytial Virus Infection;" Respiratory Care; vol. 48, No. 3; Mar. 2003; pp. 209-233.
Glanville, et al. "Intravenous Ribavirin is a Safe and Cost-effective Treatment for Respiratory Syncytial Virus Infection After Lung Transpalantation" Journal of Heart and Lung Transplantation, Mosby-Year Book, Inc., St Louis, MO, US LNKD-DOI:10.1016/J.HEALUN.2005.06.27, vol. 24, No. 12, Dec. 1, 2005, pp. 2114-2119, XP005215204 ISSN:1053-2498.
English language translation of abstract of CN 1222351, 1999.
Bonville, et al.; "Ribavirin and Cysteinyl Leukotriene-1 Receptor Blockade as Treatment for Severe Bronchitis;" Antiviral Research 69; 2006; pp. 53-59.
Wilson, et al.; "Evaluation of Salmeterol or Montelukast as Second-Line Therapy for Asthma Not Controlled with Inhaled Corticosteriods;" PubMed; http://www.ncbi.nlm.nih.gov/pubmed/11296164?ordinalpos=8&itool=EntrezSystem2.PEntrez.Pubmed.Pubmed_.

* cited by examiner

*Primary Examiner* — Elli Peselev
(74) *Attorney, Agent, or Firm* — Thomas, Kayden, Horstemeyer & Risley, LLP

(57) ABSTRACT

A method and composition for treating allergic diseases and/or airway inflammation including pollinosis, bronchial asthma, allergic rhinitis, atopic dermatitis and anaphylactic shock with the administration to a subject an amount of an anti-infectious agent such as ribavirin and optionally combined with an anti-inflammatory agent selected from inhaled steroids, leukotriene receptor antagonists and beta-2 receptor agonist.

1 Claim, 6 Drawing Sheets

(A)

(B)

(A)

(B)

(C)

(A)

(B)

METHOD AND COMPOSITION FOR TREATING ALLERGIC DISEASES

FIELD OF THE INVENTION

The present invention relates to treatments of allergic diseases. More particularly, the present invention provides methods and compositions for treating allergic diseases by use of a anti-infectious agent.

BACKGROUND OF THE INVENTION

Increasing prevalence of allergic diseases has been noted in most developed and developing countries. Allergic diseases are defamed as functional disturbances caused by type I hypersensitivity, i.e., type I immune response mediated by IgE antibodies. The symptoms include pollinosis, bronchial asthma, allergic rhinitis, atopic dermatitis, and anaphylactic shock. Today, allergic diseases tend to be more severe in civilized societies and have cost a lot of money. Among the people who are suffering from various allergic symptoms, allergic rhinitis is the most common form of allergy. Also, the attack of allergen can sometimes be fatal. According to a statistic data of 1994 conducted by he Pediatrics Department of the Medical College of National Taiwan University, the prevalence rate of allergic rhinitis among students in Taipei city (Taiwan) is over 33%, about 3 times higher than that of asthma (10~11%). The number of patient is also increasing every year. In particular, young child patients are on rapid rise. Thus, many researchers are devoting themselves in developing an improved solution to reduce economic and physical burden of the patient from such allergic diseases.

The initial stage of allergic reaction is development of IgB antibody that makes a strong combination with the mast cell or receptors on the surface of basophilic leukocyte. After the antigen or allergen being eaten by antigen-presenting cells such as macrophages, the peptide presented by MHC class II molecule on the surface of membrane is recognized by receptors on the surface of T-cell. Cell-activating substance (cytokines), such as IL-2, IFN-γ and TNF (tumor necrosis factor)-β (derived from Th1-cells), and IL-4, IL-5, IL-6, IL-9 and IL-10 (derived from Th2-cells), are produced in the activated T-cells. The produced cell-activating substance acts on T and B cells to participate in proliferation and differentiation. Then, B-cells are activated by the combination of CD40 ligand an T-cells and CD 40 on B-cells. Furthermore, as IL-4 derived from T-cells is added, B-cells are differentiated into IgB producing cells by a class switch. In the mast cells, two molecules of IgE are combined with polyvalent antigen to form a bridge on the receptors of membrane, leading to a series of biochemical processes causing degranulation. Various chemical media such as histamine are secreted from the mast cell by degranulation, and may increase the permeability of capillary, contract the smooth muscle, and enhance the mucus secretions, together with prostaglandins and leukotrienes produced newly by arachidonic acid metabolism within the membrane, which results in the followings: pruritis, flare, urticaria and angioedema on the skin; coughing, suffocating, chest tightness, respiratory difficulties and cyanosis in the respiratory tract; paling, hypotension and arrhythmia in, cardiovascular system; nausea, vomiting and diarrhea in GI tract; and paresthesia, vertigo, headache, convulsion and loss of consciousness in the nerve system.

The medicines used currently in alleviating various allergic symptoms have the problem that the effects thereof are temporary, and some side effects may occur by a long-term therapy. The antibiotics cannot affect the inhibition of IL-6 that is known for playing an important role in pathogenesis of chronic mucous exudates that are progressed in young children. It has been suggested that IL-6 could be controlled through antibiotic and steroids for a long period of time. However, administration of antibiotics and steroids for a long time may cause such side effects as suppressing immune function of the whole body.

The present inventors have made extensive clinical researches and experiments with the intention to find a novel treatment for various allergic diseases without any side effect. As a result, the inventors have found that a suitable nucleotide analog, ribavirin, possesses an excellent anti-inflammation effect without common side effects, and thus completed the present invention. In particular, the method and composition according to the present invention may increase immunity of a host to inhibit inflammation and control allergy.

SUMMARY OF THE INVENTION

The object of this invention is to provide methods and compositions for treating a subject, susceptible to or suffering from allergic diseases such as pollinosis, bronchial asthma, allergic rhinitis, atopic dermatitis, and anaphylactic shock. Thus, in one aspect, the invention provides a method of treating a subject, susceptible to or suffering from allergic diseases, comprises administering to the subject an effective amount of anti-infectious agent and optionally, an anti-inflammatory agent. In another aspect, the invention provides a pharmaceutical composition for treating a subject, susceptible to or suffering from allergic diseases, which comprises an effective amount of anti-infectious agent and optionally, an effective amount of an anti-inflammatory agent; and a pharmaceutically acceptable carrier.

In one preferred embodiment, this invention provides a method for treating allergic diseases, comprises administering to a subject an effective amount of anti-infectious agent. In this method, the anti-infectious agent is administered intranasally and the amount of the anti-infectious agent used is between 5 to 20 µg/kg of body weight of the subject. In another preferred embodiment, such method further comprises administering to the subject an effective amount of anti-inflammatory agent before, together with and/or after administering the anti-infectious agent. The anti-inflammatory agent is selected from the group consisting of an inhaled steroid, a leukotriene receptor antagonist and a β2 receptor agonist; and the amount of the anti-inflammatory agent used is between 5-10 µg/kg of body weight of the subject. Preferably, both the anti-infectious agent and the anti-inflammatory agent are administered intranasally In still another preferred embodiment, this invention provides a pharmaceutical composition for treating allergic diseases, comprises an effective amount of anti-infectious agent. In this composition, the anti-infectious agent is administered intranasally and the amount of the anti-infectious agent used is between 5-20 µg/kg of body weight of a subject. In another preferred embodiment, such composition further comprises an effective amount of anti-inflammatory agent selected from the group consisting of an inhaled steroid, a leukotriene receptor antagonist and a β2 receptor agonist. The anti-inflammatory agent can be used before, together with and/or after the anti-infectious agent, and in an amount of between 5-10 µg/kg of body weight of a subject. Preferably, both the anti-infectious agent and the anti-inflammatory agent are administered intranasally.

These and other aspects and advantages will become apparent when the Description is read in conjunction with the accompanying Examples. It is to be understood that both the foregoing general description and the following detailed description are by examples, and are intended to provide further explanation of the invention as claimed.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention. In the drawings.

DESCRIPTION OF THE INVENTION

Figure 1:
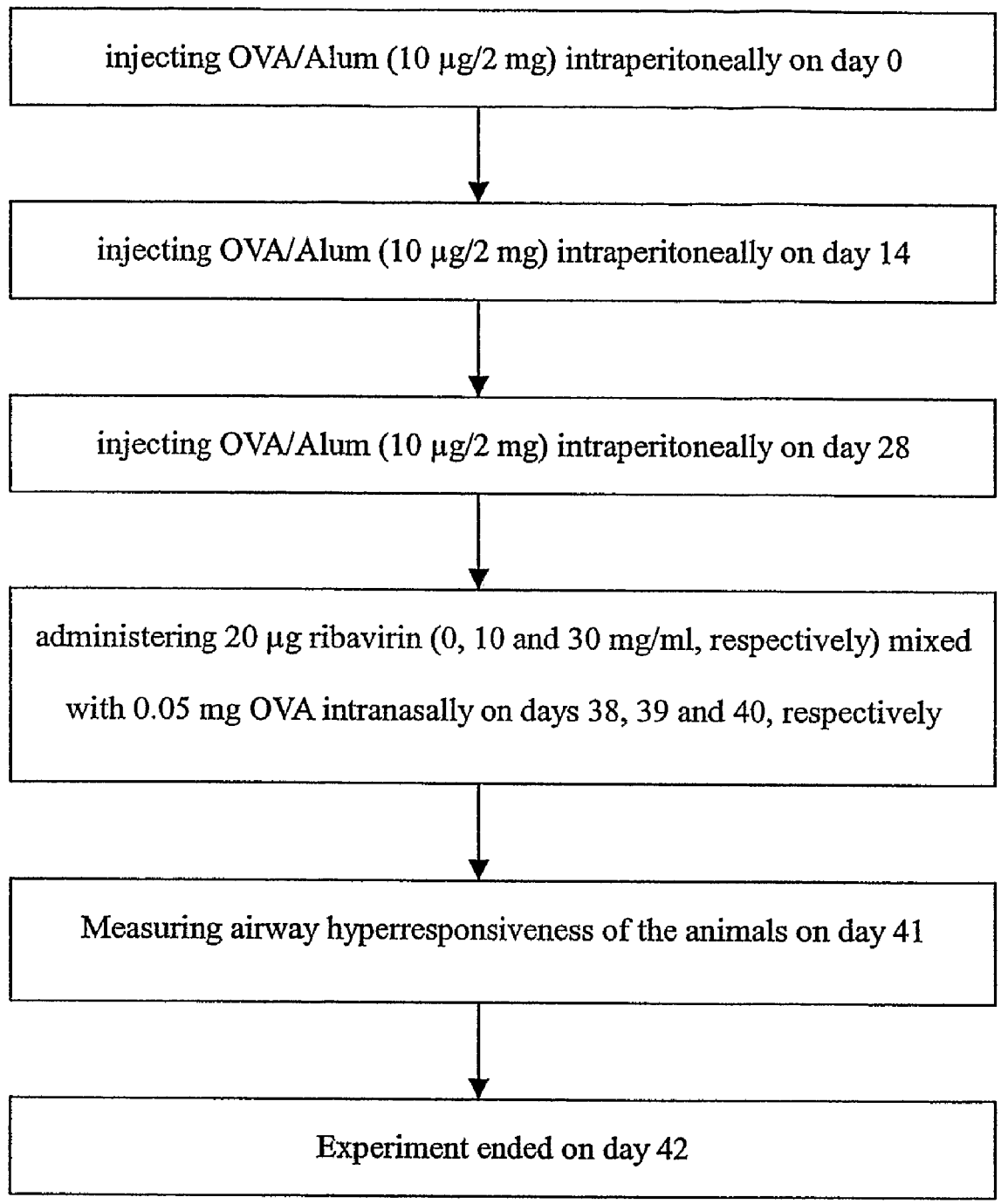
FIG. 1 illustrates the OVA protocol used in accordance with one preferred embodiment of this invention.

The embodiments described and the terminology used herein are for the purpose of describing exemplary embodiments only, and are not intended to be limiting. The scope of the present invention is intended to encompass additional embodiments not specifically described herein, but that would be apparent to one skilled il the art upon reading the present disclosure and practicing the invention.

The present invention is directed to a novel solution for treating allergic diseases such as pollinosis, bronchial asthma, allergic rhinitis, atopic dermatitis, and anaphylactic shock by use of an anti-infectious agent, and optionally, an anti-inflammatory agent. Thus, in one embodiment, this invention provides a method of treating a subject, susceptible to or suffering from allergic diseases, comprises administering to the subject an effective amount of anti-infectious agent. In one preferred embodiment, the anti-infectious agent is ribavirin.

The method may further comprise an additional step of administering an amount of anti-inflammatory agent before, together with and/or after the use of anti-infectious agent. The anti-inflammatory agent includes, but is not limited to, an inhaled steroid, a leukotriene receptor antagonist and a β2 receptor agonist. The suitable examples for the inhaled steroid includes, but is not limited to corticosteroid such as budesonide, betamethasone, dexamethasone, methylprednisolone, prednisolone, prednisone, flunisolide, triamcinolone acetonide, and fluticasone propionate. The inhaled steroid products that are commercially available are, for example, FLIXONASE, FLIXOTIDE, FLUTICASONE, PULMICORT, FLOVENT, AEROBID, AZNACORT and ADVAIR. The leukotriene receptor antagonist includes, but is not limited to, selective antagonist for BLT receptor such as SB209247, SC53228, CP195543, CGS25019C and LY293111; and selective antagonist for CysLT1 receptor such as SR2640, SKF104353, ICI204219, MK476 and LY170680. As to the β2 receptor agonist, examples include, but are not limited to, procaterol, zinterol, salmeterol, formoterol, terbutaline and fenoterol.

The anti-infectious agent and/or anti-inflammatory agent may be administered in the same or different route, including topically, orally, intranasally, intravenously or intraperitoneally. Preferably, both the anti-infectious agent and/or anti-inflammatory agent are administered directly into the respiratory tract of the subject, such as intranasal administration in the form of aerosol particles. Alternatively, the anti-infectious agent may be administered intranasally, while the anti-inflammatory agent is administered topically, orally, intravenously or intraperitoneally.

The anti-infectious agent may be administered at a dosage of from 1-50 μg/kg of body weight of a subject. A preferred range for the anti-infectious agent is a dosage of from 5-20 μg/kg of body weight of a subject, if administered intranasally. In the case when the anti-infectious agent is used together with the anti-inflammatory agent through a different route, such as, through subcutaneous injection, then the preferred dose for the anti-infectious agent is between 5-30 μg/kg of body weight of a subject.

The anti-inflammatory agent may be administered at a dosage of from 0.5 to 1 μg/kg of body weight of a subject. A preferred range for the anti-inflammatory agent is a dosage of from 5-10 μg/kg of body weight of the subject, The suitable dosage for the anti-infectious agent and the anti-inflammatory agent may be same or different, and may be further adjusted depends on the sex, age, weight, and/or history of the disease of the patient and may easily achieve by any skilled physician in this field.

The subject may be a mammal, especially a human.

A preferred embodiment of this invention provides a method of treating a subject, susceptible to or suffering from airway inflammation, comprises administering to the subject an effective amount of anti-infectious agent. The anti-infectious agent is ribavirin and the anti-inflammatory agent includes, but is not limited to, an inhaled steroid, a leukotriene receptor antagonist and a β2 receptor agonist. The suitable examples for the inhaled steroid, the leukotriene receptor antagonist and the β2 receptor lo agonist are as previously described. The preferred dosage and routes of administration for both the anti-infectious agent and the anti-inflammatory agent are also as described above.

In another preferred embodiment, the invention provides a medication that comprises aerosol particles comprising an anti-infectious agent, and optionally, an anti-inflammatory agent; and a pharmaceutically acceptable carrier. This medication is useful in treating allergic diseases such as pollinosis, bronchial asthma, allergic rhinitis, atopic dermatitis, and anaphylactic shock.

Unless defined otherwise, all technical and scientific terms used herein have the same meaning as commonly understood by one of the ordinary skill in the art to which this invention belongs. Although any methods and materials similar or equivalent to those described herein can be used in the practice or testing of the present invention, the preferred methods and materials are now described. All publications mentioned are incorporated herein by reference. Unless mentioned otherwise, the techniques employed or contemplated herein are standard methodologies well known to one of ordinary skill in the art. The materials, methods and examples are illustrative only and not limiting.

The singular forms "a", "and", and "the" are used herein to include plural referents unless the context clearly dictates otherwise. Other than in the operating examples, or where otherwise indicated, all numbers expressing quantities of ingredients, reaction conditions, and so forth used in this application are to be understood as being modified in all instances by the term "about." Accordingly, unless the contrary is indicated, the numerical parameters set forth in this application are approximations that may vary depending upon the desired properties sought to be obtained by the present invention.

EXAMPLES

The following Examples are provided to illustrate certain aspects of the present invention and to aid those of skilled in the art in practicing this invention. These Examples are in no way to be considered to limit the scope of the invention in any manner.

Animals

Female BALB/c mice were obtained and maintained in the Animal Center of the College of Medicine of National Taiwan University (Taiwan, R.O.C.). Animals were used between 6 and 10 weeks of age and were age matched within each experiment. Animal experiment protocol was approved by Animal Committee of the College of Medicine of National Taiwan University (Taiwan, R.O.C.).

Ovalbumin (OVA) Protocol for Sensitizing the Mice and Administration of Ribavirin for the Induction of Airway Hyper-responsiveness (AHR)

Mice were randomly divided into 4 groups and sensitized by an intraperitoneal injection of OVA (10 μg), which were complexed with aluminum potassium sulfate (alum, 2 mg) on day 0. All mice were boosted with another shot of OVA (10 μg) on day 14 and day 28, respectively. The mice in the negative control group were injected with phosphate buffer solution (PBS). As to the mice in the rest three groups, each group received 20 μl of 0, 10 or 30 mg/ml ribavirin together with intranasal challenge of 0.05 mg of OVA on days 38-40, respectively. AHR for mice in each group was measured on day 41, and all mice were bled and sacrificed on day 42, when the experiment ended. FIG. 1 illustrated the timeline of the above-identified OVA protocol used in this study.

Measurement of AHR

Figure 2:
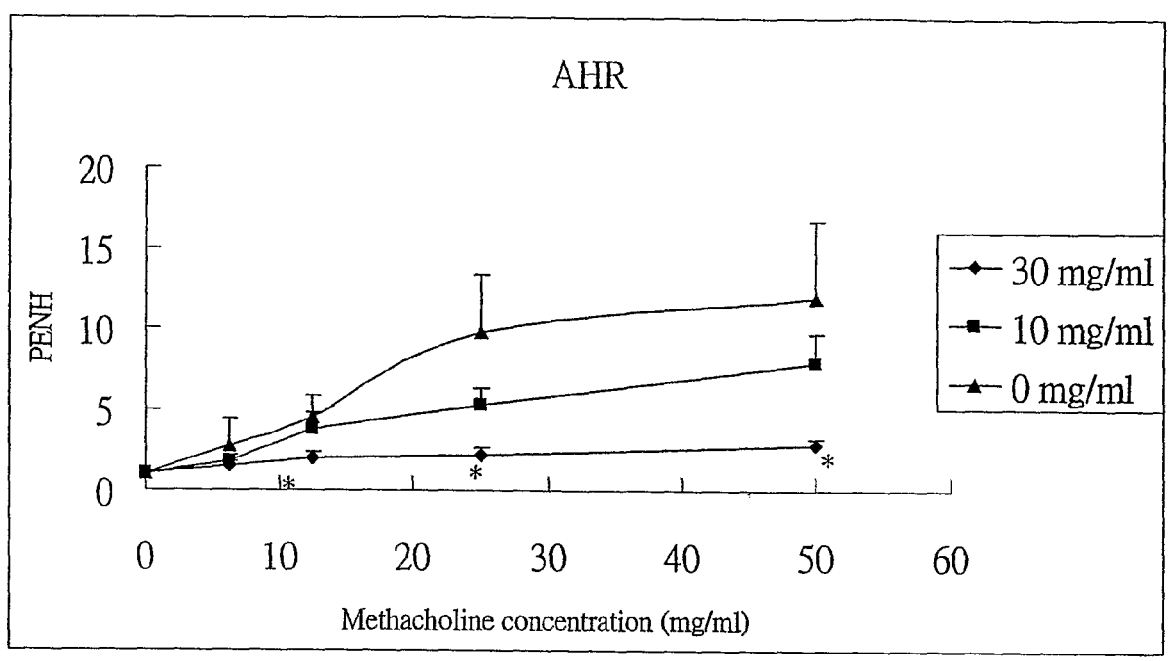
FIG. 2 illustrates the effects of ribavirin on Moh-induced airway responsiveness in OVA-sensitized mice in accordance with one preferred embodiment of this invention, various concentration of ribavirin were given intranasally (0, 10, 30 mg/ml) after the challenge of OVA, results were expressed as the mean +s.e.m. with 5 mice in each group, experiments were repeated 3 times with similar results, *P<0.05 as compared with the control group (without ribavirin treatment)

The effect of ribavirin on airway responsiveness to aerosolized methacholine (Mch) in OVA-sensitized mice were assessed by the following procedures. First, mice were sensitized with OVA according to the procedure described in Example 1.1, then increasing concentrations of Mch (0, 6.25, 12.5, 25 and 50 mg/ml, respectively) with or without ribavirin (the positive control mice were treated with saline, whereas the rest of the mice were treated with 10 or 30 mg/ml ribavirin, respectively) were given to the animal intranasally, and whole-body plethysmography were then measured by taking the readings of pressure differences between the main chamber of the plethysmography, which contained the animal, and a reference chamber. Each reading was taken for 3 minutes and averaged for the entire time course after nebulization. Calculated Data were expressed as the fold increases above saline challenge baseline values using the dimensionless parameter Penh as described. Results were illustrated in FIG. 2. It is evident from FIG. 2 that Penh increased as the concentration of Mch increased) and mice sensitized with OVA but without any ribavirin treatment developed marked increased airway responsiveness to Mch challenge. Intranasal administration of ribavirin inhibited the increase in airway responsiveness to Mch in OVA-sensitized mice as compared with that cf the PBS-treated mice.

Therapeutic Effect of Ribavirin On Airway Eosinophilic Inflammation

Figure 3:
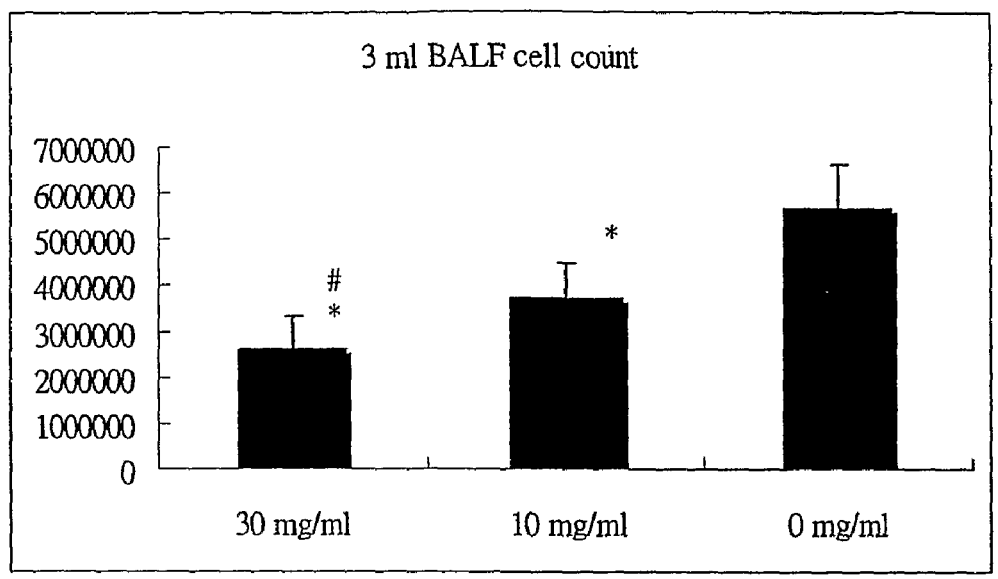
FIG. 3 are bar graphs illustrating the effects of ribavirin on cell infiltration in mice's airway, in which (a) is the effect of ribavirin on total cell number in 3 ml BAL fluid and (b) is the effect of ribavirin on the cell number of respective cell types including monocytes, neutrophils, eosinophils and lymphocytes; experiments were repeated 3 times with similar results, *P<0.05 and #P<0.01 as compared wit the control group (without ribavirin treatment)
Figure 3:
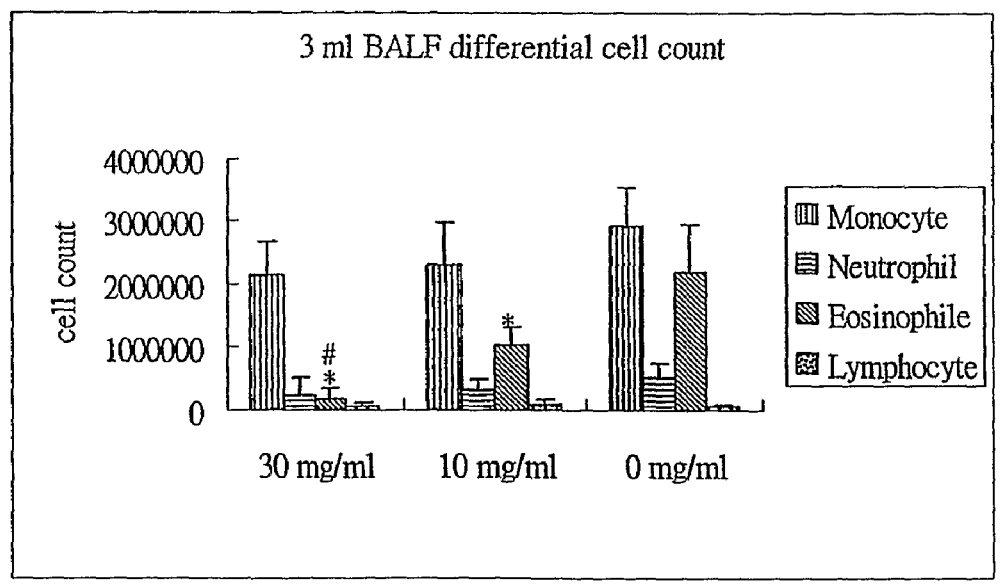

Whether ribavirin could alleviate airway inflammation in OVA-sensitized mice was determined by analyzing the cellular composition in the bronchoalveolar lavage (BAL) fluid of the sensitized mice 48 hours a the last challenge. In brief, all groups of OVA sensitized mice were bled from the retroorbital venous plexus and sacrificed. The lung was immediately lavaged via the trachea cannula with 3×1 ml of HBSS, free of ionized calcium and magnesium. The lavage fluid was centrifuged at 400 xg for 10 minutes at 4° C. After washing, the cells were resuspended in 1 ml HBSS and total cells counts were determined by use of a hemocytometer. Cytocentrifuged preparations were stained with Liu's stain for different cell counts. A minimum of 200 cells was counted and classified as macrophages, lymphocytes, neutrophils and eosinophils, based on standard morphological criteria. Results were illustrated in FIG. 3. It is found that exposure to intranasal OVA often induced a marked increase in the number of neutrophils and eosiniphils in BAL fluid for the mice in positive control group (FIG. 3). On the contrary, treatment of ribavirin (10 or 30 mg/ml) decreased not only the total cell counts (FIG. 3A), but also the number of respective cell types including monocytes, neutrophils, and eosinophiles (FIG. 3B).

Figure 4:
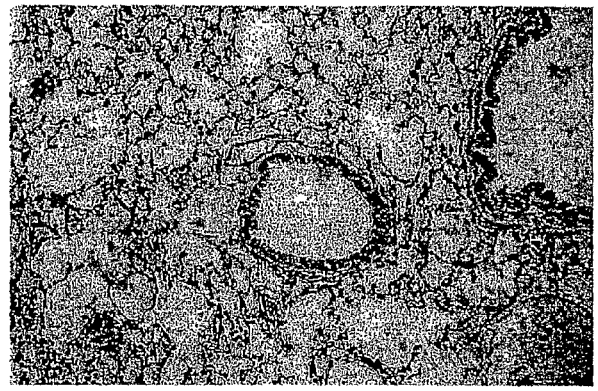
FIG. 4 are photographs showing the morphology of lung tissue of OVA-sensitized mice treated with or without ribavirin, ill which (A) is the phase contrast photograph showing lung tissue of OVA-sensitized nice after treating with 30 mg/ml ribavirin, (B) is the he phase contrast photograph showing lung tissue of OVA-sensitized mice, after treating with 10 mg/ml ribavirin, and (C) is the picture of lung tissue of OVA-sensitized mice without any ribavirin treatment, the tissue sections were stained with hematoxylin and cosin and were examined by light microscope (original magnification=400×)
Figure 4:
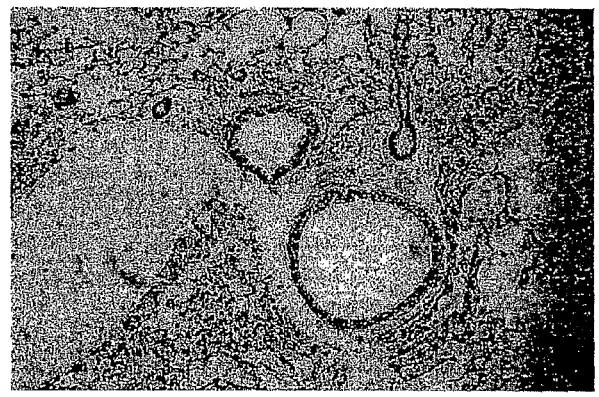
Figure 4:

After the lavage, the lungs were immediately removed and fixed in 10% neutral-buffered formalin, routinely processed, and embedded in paraffin wax. Five-micrometer sections were prepared and stained with hematoxylin md eosin, and subsequently examined by the light microscope, results were provided in FIG. 4. It is clear that ribavirin (FIGS. 4a and 4b, 30 and 10 mg/ml, respectively) could efficiently inhibit the infiltration of the cells and reduce the pathological damage within the lung in this OVA-sensitized model.

Therapeutical Effects of Ribavirin on Chemokines Levels it BAL Fluid

Figure 5:
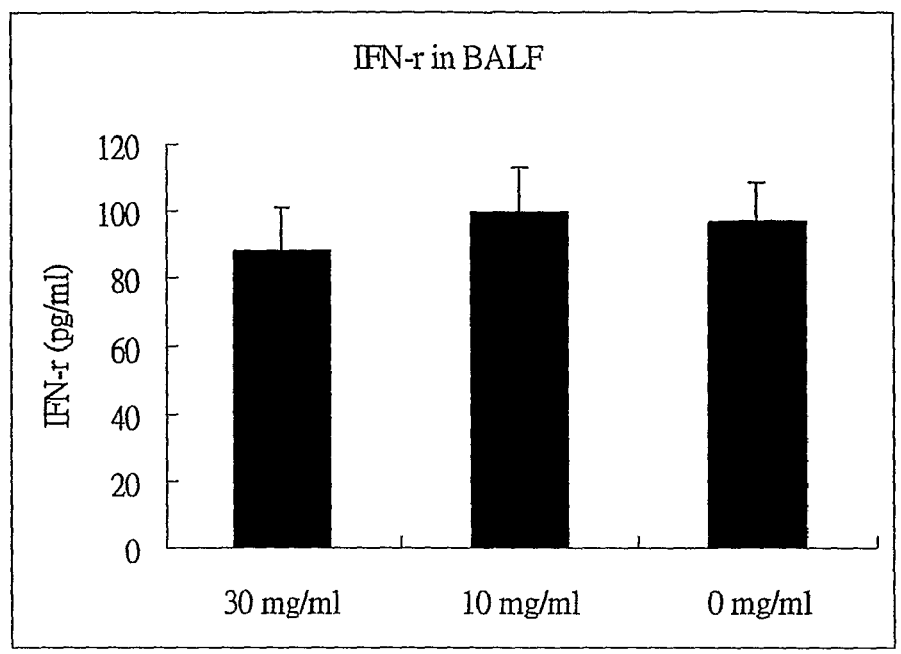
FIG. 5 illustrates the levels of INF-γ (a), IL-4 (b), KC (c) and eotaxin (d) in BAL fluid of mice of example 1.1 as measured by ELISA experiments were repeated 2 times with similar results, *P<0.05 as compared with the control group (without ribavirin treatment).
Figure 5:
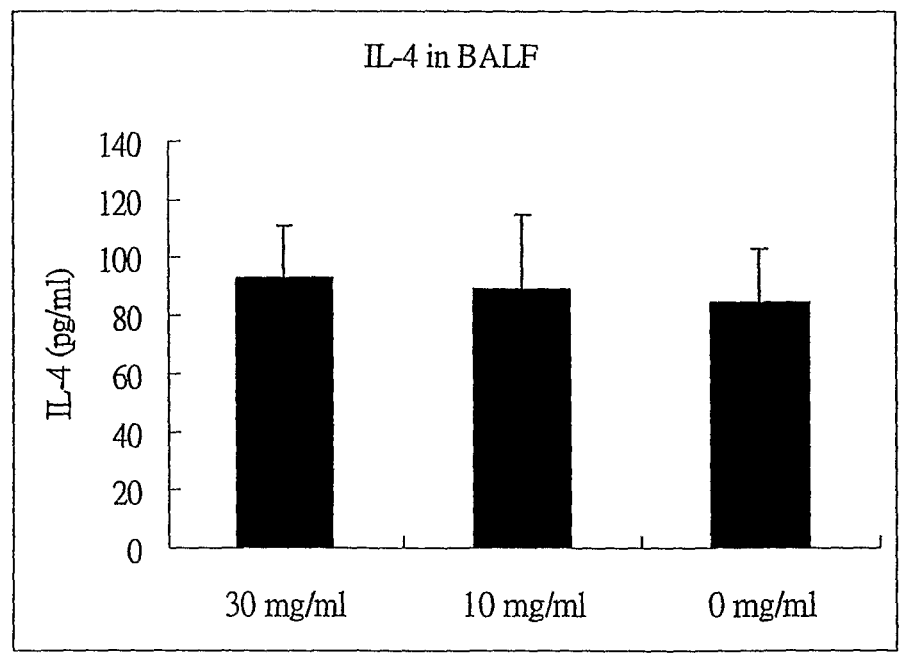
Figure 5:
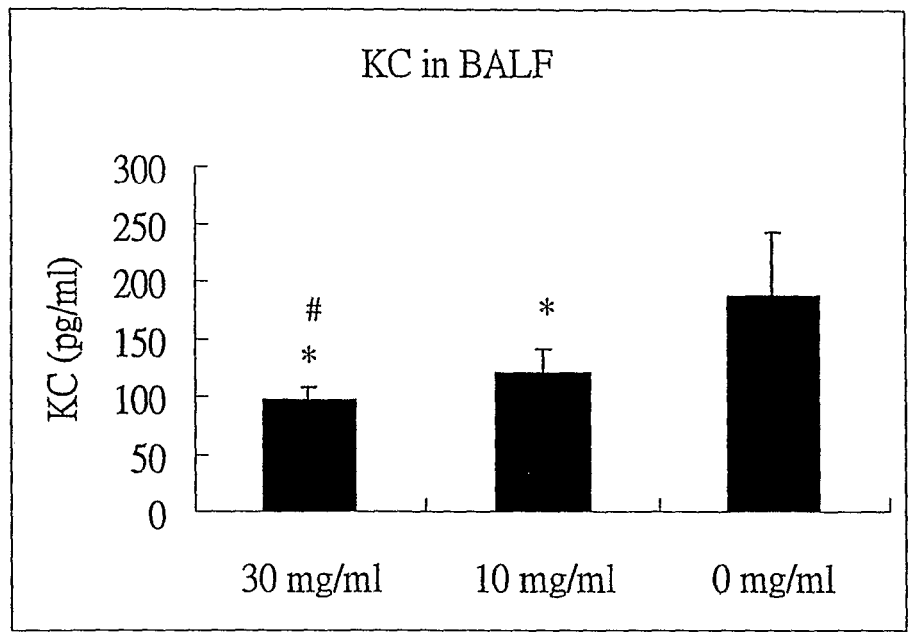
Figure 5:
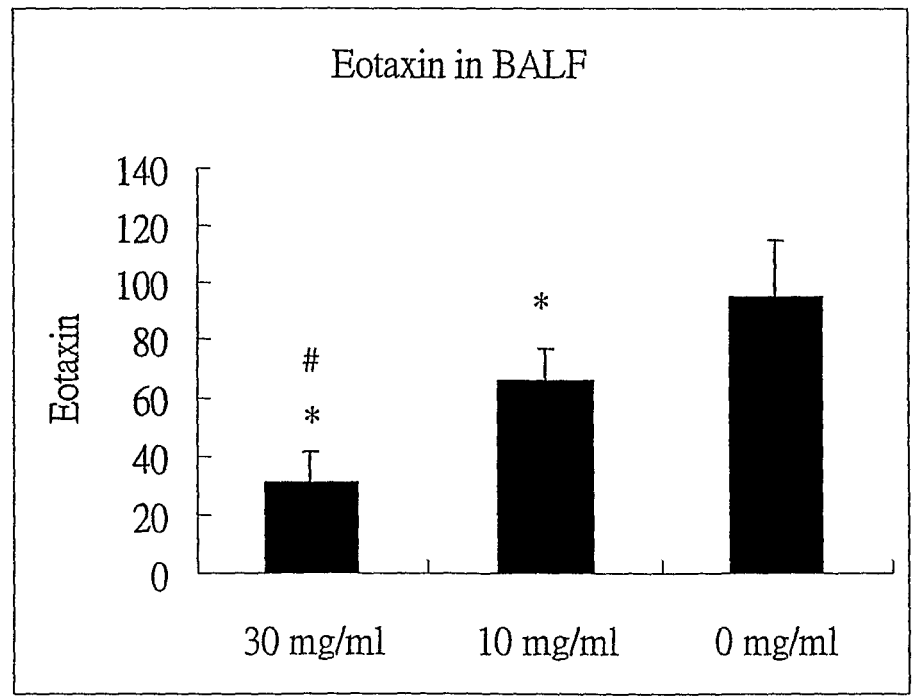

OVA-sensitized mice were lavage according to the procedure described above, and the levels of chemokines were assayed by an ELISA kit (R&D) in accordance with the manufacturer's instructions. Take the measurement of eotaxin as an example, the BAL fluid was collected and added to wells precoated with anti-eotaxin antibodies over night at 4° C. After incubation for 2 hours, the plates were washed and biotin-conjugated antibodies were added. After two more hours at room temperature, HRP-avidin was then added, and the OD (at 450 nm) values were converted to concentrations of eotaxin in the BALF. The level of other chemokines including KC, IL-4 and INF-γ may be measured according to similar procedures. Results were illustrated in FIG. 5.

It is found that the level of IF-γ (FIG. 5a) and IL-4 (FIG. 5b) in OVA-sensitized mice were not affected by ribavirin, however, both the level of eotaxin (FIG. 5*d*) and KC (FIG. 5*c*) were significant reduced upon administration of ribavirin. The results suggested that ribavirin does possess a therapeutic effect, on the airway inflammation in asthma.

INDUSTRIAL APPLICABILITY

It is an advantage of the present invention that it provides a novel solution for treating allergic diseases by use, of an anti-infectious agent, and optionally, an anti-inflammation agent. The method and composition according to the present invention may increase immunity of a host to inhibit inflammation and control allergy and thereby provides treatment to allergic diseases such as pollinosis, bronchial asthma, allergic rhinitis, atopic dermatitis, and anaphylactic shock.

The foregoing description of various embodiments of the invention has been presented for purpose of illustration and description. It is not intended to be exhaustive or to limit the invention to the precise embodiments disclosed. Numerous modifications or variations are possible in light of the above teachings. The embodiments discussed were chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, ad equitably entitled.

The invention claimed is:

1. A method of treating a subject suffering from pollinosis, bronchial asthma, or allergic rhinitis, comprising administering intranasally to the subject an amount of ribavirin between 5-20 µ/kg of body weight of the subject per day.

* * * * *